United States Patent [19]
Herrmann

[11] Patent Number: 5,531,850
[45] Date of Patent: Jul. 2, 1996

[54] APPARATUS AND METHOD FOR APPLYING TRANSVERSE TENSIONED ELASTIC

[75] Inventor: Thomas R. Herrmann, Federal Way, Wash.

[73] Assignee: Paragon Trade Brands, Inc., Federal Way, Wash.

[21] Appl. No.: 263,872

[22] Filed: Jun. 21, 1994

[51] Int. Cl.⁶ ............................ B65H 57/28; B32B 31/06
[52] U.S. Cl. .......................... 156/161; 156/164; 156/176; 156/177; 156/267; 156/439; 156/440; 156/496; 156/516
[58] Field of Search ...................... 156/176, 177, 156/178, 161, 164, 436, 439, 440, 495, 496, 267, 516; 28/100, 101

[56] References Cited

U.S. PATENT DOCUMENTS

| | | | |
|---|---|---|---|
| 1,923,710 | 8/1933 | Collings et al. | 156/440 |
| 3,321,348 | 5/1967 | Rupp | 156/177 |
| 3,649,411 | 3/1972 | Bolles | 156/177 X |
| 3,728,191 | 4/1973 | Wierzba et al. | |
| 3,771,330 | 11/1973 | Carman | 28/100 X |
| 4,284,454 | 8/1981 | Joa | |
| 4,523,969 | 6/1985 | Spencer | |
| 4,642,151 | 2/1987 | Coenen | |
| 4,726,874 | 2/1988 | VanVliet | |
| 4,776,911 | 10/1988 | Uda et al. | |
| 4,786,346 | 11/1988 | Ales et al. | |
| 4,908,089 | 3/1990 | Uda et al. | 156/439 |
| 4,925,520 | 5/1990 | Beaudoin et al. | |
| 4,933,038 | 6/1990 | Liu | 156/440 X |
| 5,000,806 | 3/1991 | Merkatoris et al. | |
| 5,043,036 | 8/1991 | Swenson | |
| 5,209,801 | 5/1993 | Smith | 156/177 X |
| 5,221,390 | 6/1993 | Persson et al. | 156/177 X |
| 5,380,388 | 1/1995 | Montagne et al. | 156/177 X |

*Primary Examiner*—Jeff H. Aftergut
*Attorney, Agent, or Firm*—Klarquist, Sparkman, Campbell, Leigh & Whinston

[57] ABSTRACT

An apparatus in which material to have elastic applied thereto is carried by a first conveyor in one direction along a flow path. An elastic conveyor extending transversely of the material flow path is operable to continuously draw elastic from storage, tension it and carry it to a feeder head that reciprocates transversely of the flow path. A transverse elastic applicator receives elastic substantially continuously from the feeder head in a square-wave pattern and moves it toward the flow path. The elastic applicator has spaced guide members mounted adjacent opposite sides of the flow path to hold tensioned elastic therebetween extending transversely of the flow path as the elastic applicator moves the elastic to the flow path and applies the elastic to the material on the first conveyor. Cutters positioned inboard of the guide members sever the elastic after it has been applied to the material.

27 Claims, 7 Drawing Sheets

APPARATUS AND METHOD FOR APPLYING TRANSVERSE TENSIONED ELASTIC

BACKGROUND AND SUMMARY OF THE INVENTION

The present invention relates to apparatus and method for applying tensioned elastic to material, and more specifically to apparatus and method for applying elongate tensioned elastic members transversely to a moving web of material.

The application of elongate tensioned elastic extending transversely of a moving flow path has been less than completely satisfactory with previously known apparatus and methods. Many previously known devices and methods have used apparatus which requires that the moving web of material stop, or slow down substantially, and then start, or speed up, again to permit transference of the elastic onto material. Other methods and equipment may permit a material web to run continuously, but only at relatively low speeds. Yet others use apparatus and methods which may provide adequate operation for applying tape-like materials, but are less desirable for applying tensioned elastic strands.

A general object of the present invention is to provide novel apparatus which permits high-speed application of elongate elastic transverse onto a high-speed continuously moving material web.

More specifically, an object of the invention is to provide apparatus in which material to have elastic applied thereto is carried by a first conveyor in one direction along a flow path. An elastic conveyor extending transversely of the material flow path is operable to continuously draw elastic from storage, tension it and carry it into a position extending transversely of and spaced from the flow path. A transverse elastic applicator positioned adjacent the first conveyor receives elastic substantially continuously from the elastic conveyor and moves it toward the flow path. The elastic applicator has spaced guide members mounted adjacent opposite sides of the flow path to hold tensioned elastic extending therebetween and transversely of the flow path. The guide members are also operable to hold the tensioned elastic in position as the elastic applicator moves the elastic to the flow path and applies the elastic to the material on the first conveyor. Cutters positioned inboard of the guide members sever the elastic from the guide members after it has been applied to the material.

Another object of the present invention is to provide novel apparatus in which elongate tensioned elastic can be substantially continuously provided extending transversely of a moving web of material which may be used to produce a garment. The apparatus is suitable for application of elastic at high working speeds without the need for interruption or intermittent operation of the moving web of material. It is especially well adapted for the application of the waist zone elastics to disposable diapers or similar products. Such apparatus comprises an elastic feeder positioned adjacent the elastic applicator and operable to receive elastic from the elastic conveyor. The feeder has a feeder head reciprocatively movable in a feeder path extending transversely of the flow path and cooperable with the movement of the elastic applicator to thread elastic onto the applicator in a continuous "square wave" pattern.

Another object of the invention is to provide a novel method for applying elongate tensioned elastic to material moving in one direction along a flow path with the elastic extending transversely of the flow path. The method includes the steps of drawing an elongate section of elastic from a quantity of elastic, stretching the section of elastic to a desired tension, and feeding the elastic reciprocatively in transverse portions between opposed first and second ends of a feeder path that is oriented substantially transversely of the flow path. The elastic is alternately grasped in first and second elastic end regions, respectively, adjacent the first and second feeder path ends as the elastic is fed adjacent the first and second feeder path ends while simultaneously moving the grasped first and second end regions toward the flow path. Movement of the grasped first and second end regions is halted when the elastic is fed transversely across the feeder path between the opposing first and second feeder path ends. The transverse portions are deposited onto the material and cut inboard of the grasped first and second end regions.

These and other objects and advantages will become more apparent as the following description is read in conjunction with the drawings.

DESCRIPTION OF PREFERRED EMBODIMENTS OF THE INVENTION

Figure 1:
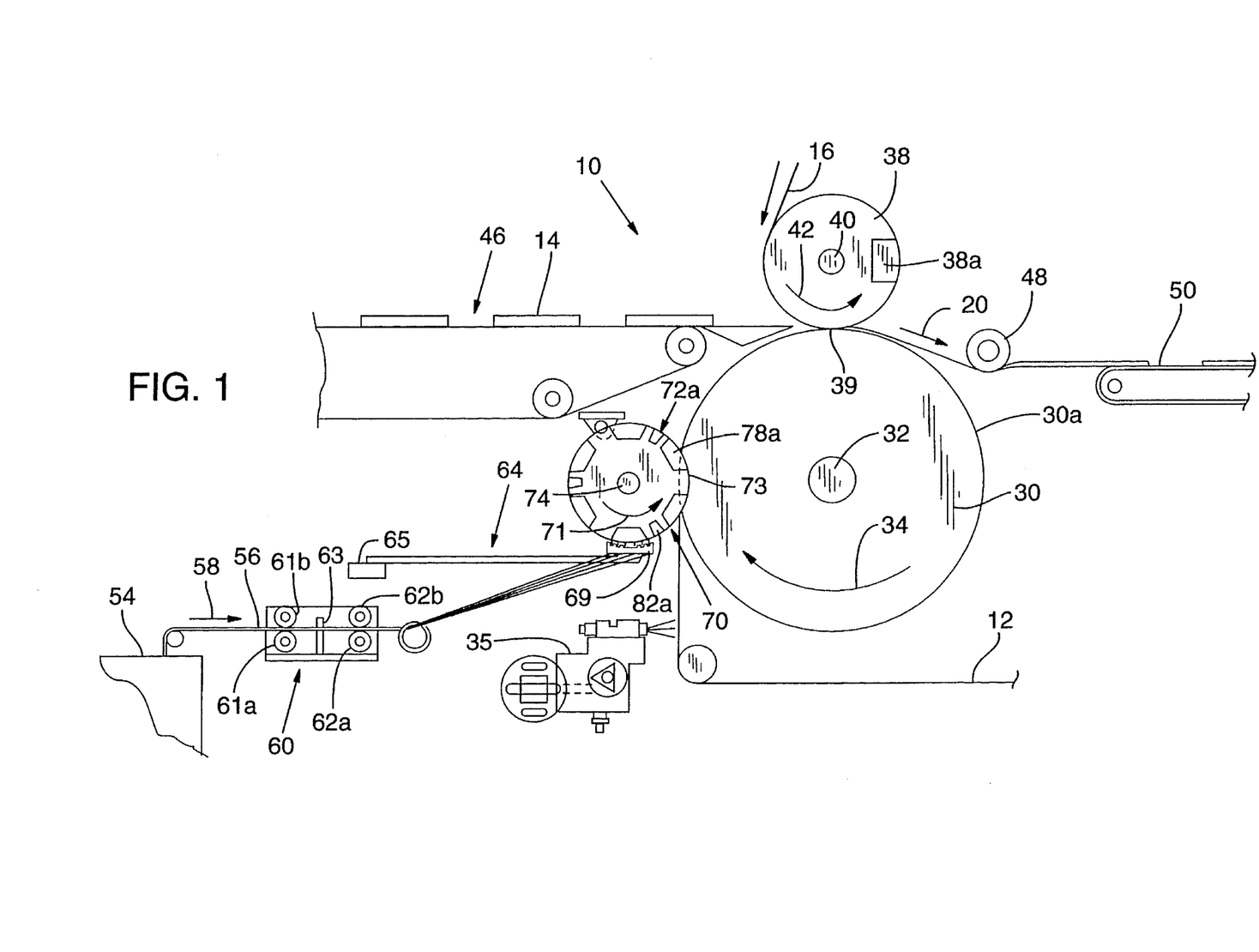
FIG. 1 is a schematic side elevation view of apparatus constructed according to an embodiment of the invention in which the method of the invention is practiced.
Figure 2:
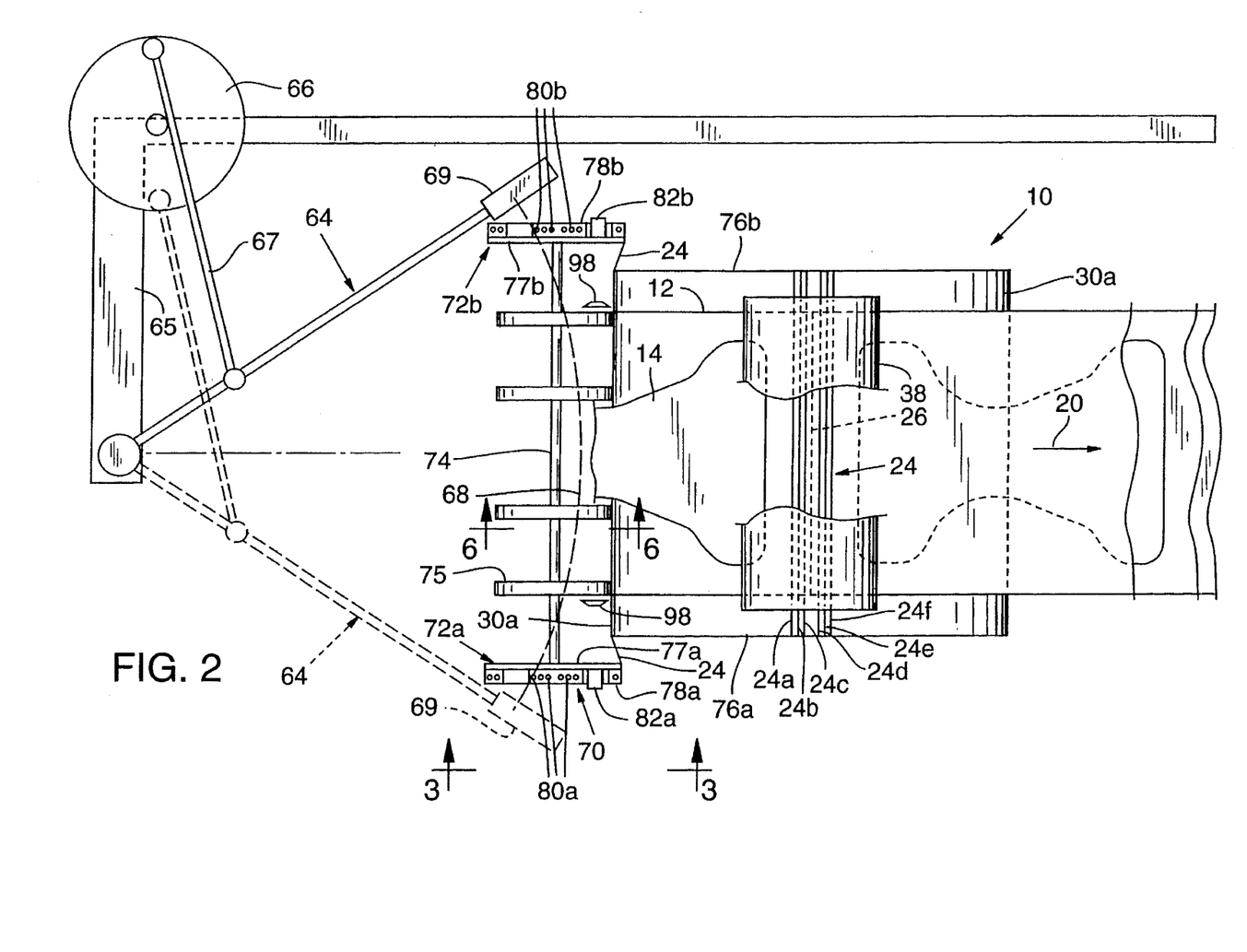
FIG. 2 is a top plan view of the apparatus illustrated in FIG. 1, with portions cut away for clarity of illustration.

Referring first to FIGS. 1 and 2, at 10 is indicated generally apparatus constructed according to an embodiment of the invention. The apparatus is illustrated specifically in use to produce disposable diapers or training pants, but it should be understood that it is not limited to such products.

As is known, disposable diapers and training pants generally include an outer, or backing, sheet of a liquid impervious material, onto which an absorbent pad is placed. A liquid pervious liner, or inner, sheet is placed thereon to encase the absorbent pad therebetween. One such garment and method of manufacture is illustrated in U.S. Pat. No. 4,726,807 to Young and Lancaster, which is herein incorporated by reference to illustrate typical materials used and known methods of manufacturing such garments.

In the manufacture of such products it is often desirable to be able to provide strands, or bands, of elastic material extending transversely of the inner and outer sheets to produce elasticized waist areas for the garment produced. Since such products often are manufactured on assembly lines in which the garment material moves substantially continuously longitudinally, in what is referred to as the "machine direction," the elastic must be placed on a moving web with the elastic stretched and extending transversely of the machine direction.

Referring to FIGS. 1 and 2, an elongate sheet, or web, of backing material 12 having a selected width is moved by a first conveyor in a flow path direction 20. An elongate absorbent pad 14 is placed thereon, and an elongate sheet of inner liner material 16 is laid thereover. As is seen in FIG. 2, the flow path direction 20 is generally longitudinally, or in a machine direction, for the garments to be produced.

As an example of materials which may be used to produce a garment, the liquid impervious back sheet 12 may be a thin thermoplastic material, such as a pigmented polyethylene film having a thickness in the range of 0.02–0.04 mm. The liquid pervious liner sheet 16 may be a carded polyester fiber with a latex binder or of a spun-bonded polypropylene having continuous fibers and thermally bonded by patterned calendar rolls. The liner sheet may be impregnated with a surfactant to render it hydrophilic. The moisture absorbent layer, or pad, 14 may be of wood fibers or other fibers, such as chemical wood pulp, or any other suitable liquid absorbing material such as commercially available fluff pulp or a fluffed bleached craft soft wood pump.

A series of elongate elastic elements 24, herein shown as individual elastic bands 24a, 24b, 24c, 24d, 24e, 24f extend transversely of the flow path 20 and are adhered to backing material 12. A dashed line 26 (see FIG. 2) positioned between the three elastic bands 24a, 24b, 24c and the other three bands 24d, 24e, 24f indicates a transverse cut-off line at which one garment will be severed from the following garment in the manufacturing process. The elastic bands provided will serve to elasticize the waist regions of garments produced.

Describing the apparatus, and referring still to FIGS. 1 and 2, it includes a circular conveying drum 30 which is supported on and driven about a central axle 32. The direction of rotation is indicated generally by arrow 34. The peripheral outer surface 30a of the drum supports backing material 12 as it travels from the bottom side of the drum to the top side of the drum in FIG. 1. As is seen in FIG. 2, the drum is wider than the usual width of material to be carried thereon so that it can accommodate sheet material of different widths.

An adhesive spray device, as indicated generally at 35, is positioned below the drum conveyor 30 to spray a coating of adhesive material onto the side of the backing material sheet 12 that receives the elastic bands 24a–24f. The adhesive applicator 35 is preferably spaced from the drum conveyor to prevent accumulation of any possible overspray on the drum. The adhesive may be applied over the entire outward width of the backing material sheet 12 to provide adhesion for the bands 24a–24f and absorbent pads 14.

An elongate upper drum 38 is mounted for powered rotation on an axle 40 substantially parallel to axle 32 in the direction indicated by arrow 42. Drum 38 carries the liner sheet 16 into position adjacent and overlying the backing sheet 12, pads 14, and elastic bands 24a, 24b, 24c, 24d, 24e, 24f. Drum 38 has an external contour which will not substantially compress absorbent pad 14, but does have a bumper section 38a extending substantially fully across the length of drum 38 which presses materials tightly at nip 39 between drum 38 and drum 30. This serves to press the backing and liner material tightly together over the elastic bands.

A pad conveyor 46 is operable to carry longitudinally spaced pads 14 and insert them into the space between backing sheet 12 and liner sheet 16, such that a pad will be carried by the backing and liner sheets through nip 39 and be captured between the two sheets. The spacing between longitudinally moving pads 14 is such that they are positioned between elastic bands 24 deposited on backing material 12.

The combined backing and liner sheets with an absorbent pad encased therebetween are carried downstream, to the right in FIGS. 1 and 2, and are supported on a subsequent roller 48, and other conveyor mechanism 50 in the system as they are moved therealong.

Referring now more specifically to the apparatus for applying elastic strands and referring to FIG. 1, an elastic storage container is indicated generally at 54. An elongate strip of elastic material 56 is drawn from container 54 and carried by an elastic conveyor in the direction of arrow 58. The elastic strip material already has been scored during its manufacture, such that it is easily split into multiple elastic bands, or strands. In the following, reference numeral 24 refers to such bands collectively, and the numerals 24a, 24b, 24c, 24d, 24e, 24f refer to individual bands.

An example of the elastic used is 0.015 inch by 0.027 inch three-end natural rubber obtained from Fulflex. Two such elastics are used to produce the six bands preferred in the invention. However, the elastic may be any form of elasticized material which may be found to be desirable for producing the product at hand. Examples of other materials which might be used are polyurethane, ribbon elastic, Lycra strands, or others used in the industry.

A splitter device which separates the scored elastic strip into multiple strands and also provides initial tensioning of the strands is indicated generally at 60 (See FIG. 1). This splitter device includes a first pair of rollers 61a, 61b positioned one above the other, between the nip of which strip 56 is moved. A second set of powered rollers 62a, 62b, are positioned one above the other and downstream from rollers 61a, 61b with the elastic bands extending through the nip between rollers 62a, 62b. Rollers 62a, 62b are driven at a speed greater than rollers 61a, 61b such that tension is imparted to the elastic bands and they are stretched, or tensioned, to a desired degree. A plurality of spaced pins 63 are disposed intermediate rollers 61a, 61b and 62a, 62b with the elastic bands being routed about the pins to separate strip 56 into the six individual bands 24a–24f.

The bands 24a–24f are routed through an elastic feeder head 69, which is described in detail below. The feeder head is mounted at the free end of a swing arm 64 that is pivotally mounted to a frame member 65. The swing arm 64 may be driven by a variety of mechanisms, such as an eccentric drive 66 and connecting rod 67 mechanism. The swing arm 64 reciprocatively swings the head 69 through an arcuate feeder path 68 (see FIG. 2) that is generally horizontal and transverse to the flow direction 20. The arcuate path 68 extends along an intermittently rotating elastic applicator 70, which will now be described.

Figure 3:
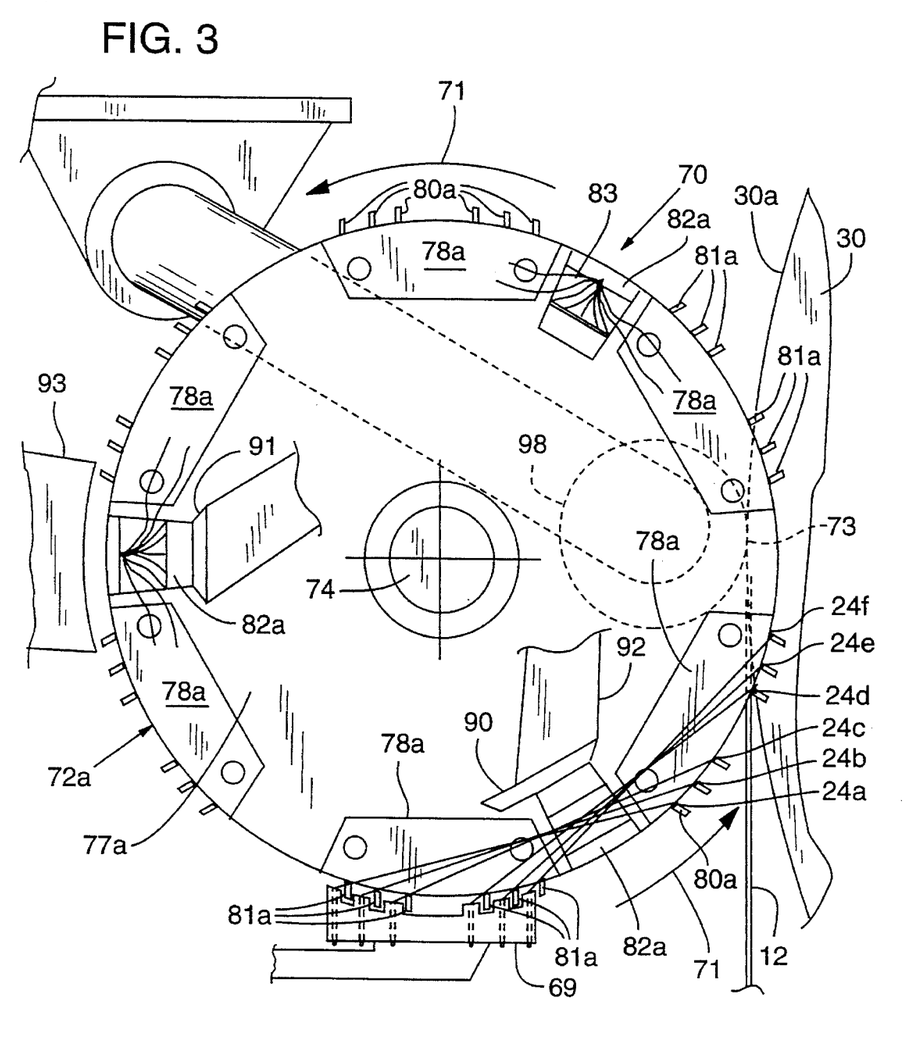
FIG. 3 is an enlarged end view taken generally along the line 3—3 in FIG. 2.

The bands 24a–24f extend from the feeder head 69 for threading onto the elastic applicator 70. The elastic applicator 70 rotates in the direction of arrow 71 to carry the threaded elastic bands through an applicator path for deposit on the backing sheet 12 at a nip 73 between the applicator and drum 30. As best shown in FIGS. 1–3, the applicator 70 has a generally cylindrical shape, with opposing end wheels 72a, 72b mounted for rotation on an axle 74. A plurality of pressure discs 75 are mounted on the axle intermediate the end wheels. The axle 74 extends substantially parallel to the conveying drum central axle 32.

As shown in FIG. 2, the applicator end wheels 72a, 72b are spaced outwardly from the opposing ends 76a, 76b of the drum 30, and have forward edges which are offset slightly forwardly of the portion of the drum face 30a nearest the applicator 70.

The pressure discs 75 have a slightly smaller diameter than the end wheels 72a, 72b, so that they may contact the drum face 30a (as described below). The slight forward offset of the end wheels helps ensure snug tensioned application of the bands 24 onto backing sheet 12.

The following description of end wheel 72a, as shown in FIG. 3, applies equally to opposing end wheel 72b. Identical elements of the end wheels 72a, 72b will have identical reference numerals, except for the appropriate substitution of the letters "a" or "b".

The end wheel 72a has a base plate 77a that peripherally supports six guide blocks 78a and three lock blocks 82a. The lock blocks 82a are each mounted between alternating pairs of adjacent guide blocks 78a. Six spaced apart pin-like guide members (corresponding to the six bands 24a–24f) are mounted on each guide block 78a to extend substantially radially from the periphery of the end wheel 72a. The set of guide members mounted on guide blocks 72a that lead lock blocks 82a as the wheel 72a rotates in path direction 71 are designated as leading guide members 80a. The guide members mounted on guide blocks 78a that trail lock blocks 82a are referred to as trailing guide members 81a.

The guide members 80a, 80b, 81a, 81b and lock blocks 82a, 82b will now be further described relative to weaving of the elastic bands 24a–24f onto the applicator 70. Such weaving is best appreciated by reference to FIG. 7, which shows the paths traced by the guide members and the lock blocks as if they were extended from their circular to a planar orientation. It should be recognized that in operation the parts on the applicator are moving in the direction of arrow 71, while feeder head moves only transversely along arcuate paths 68.

Figure 7:
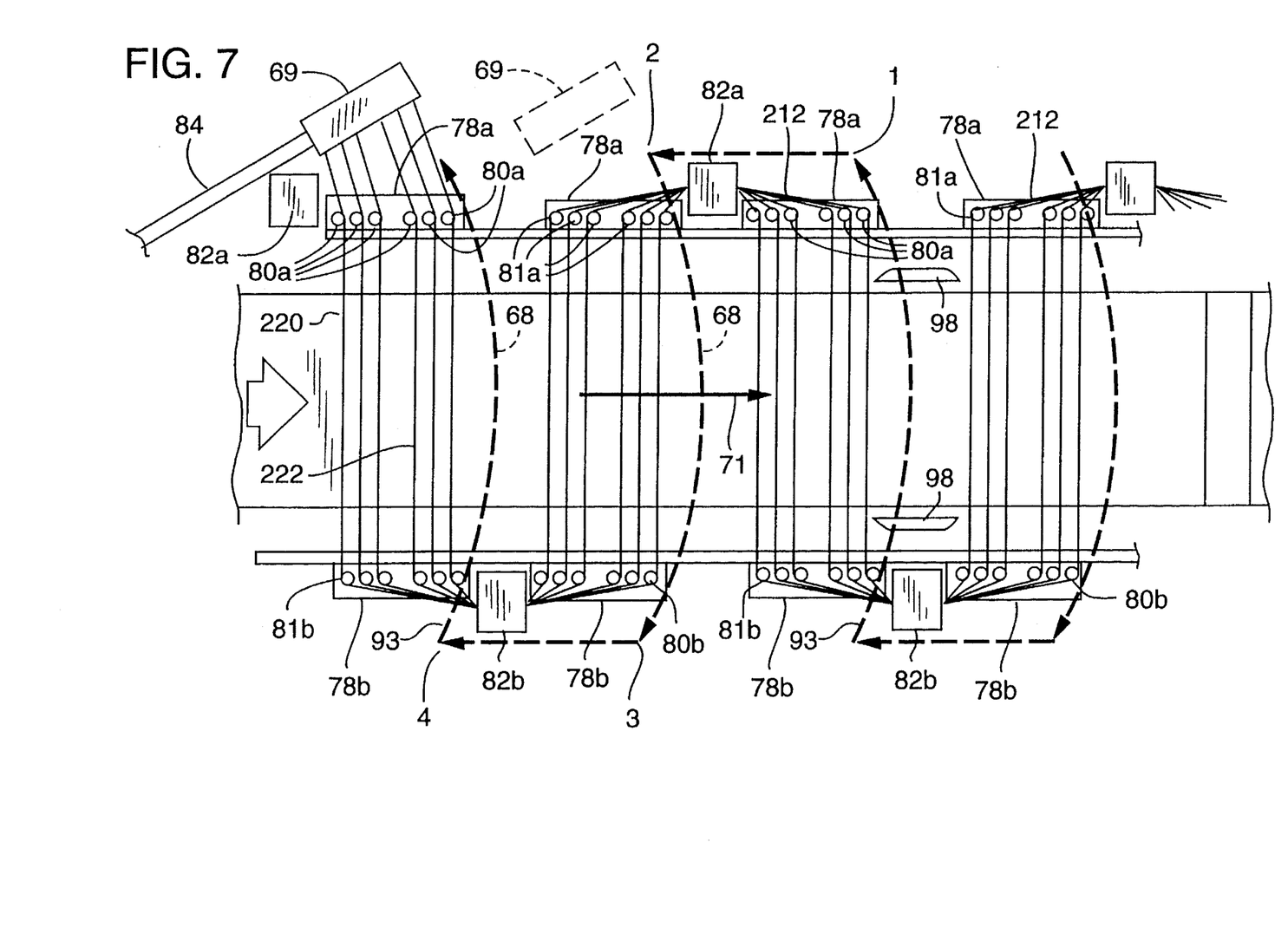
FIG. 7 is a somewhat schematic illustration of the weaving of elastic bands in accordance with an aspect of the invention.

Positions 1, 2, 3, 4, and 5 indicate positions of the feeder head 69 relative to the applicator through the weaving of one "square wave" cycle of elastic onto the applicator. Movement from positions 1 to 2, and 3 to 4 occurs by the applicator 70 rotating through 60 degree intervals while the feeder head is swung to either of its farthest outboard positions at opposed ends of the arcuate path and then returns toward the applicator. Movement from positions 2 to 3, and 4 to 5 occurs by the feeder head moving through the arcuate feeder path 68 while the applicator remains substantially stationary. In other words, the positions 1–5 follow the feeder head 69 as it threads the bands 24a–24f from leading guide members 80a, through a lock block 82a, around trailing guide members 81a, along the arcuate path 68, around leading guide members 80b, through the lock block 82b, and around trailing guide members 81b. In the description, "upstream" and "downstream" will be relative to the direction of applicator rotation 71.

At position 1, the feeder head 69 is positioned at one outboard end of the arcuate path 68, with the bands 24a–24f having been threaded through the leading set of members 80a. While the head 69 is positioned outboard of the wheel 72a, the applicator 70 rotates through a 60 degree interval in path direction 71 to thread the bands through lock block 82a, which will now be described.

Figure 5A:
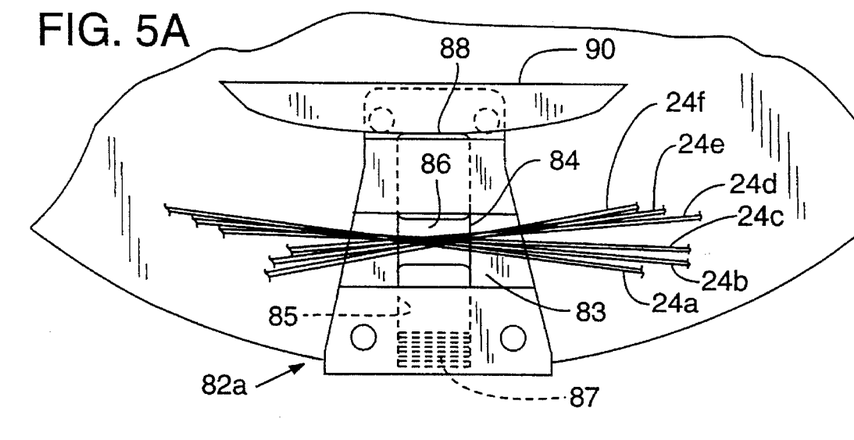
FIGS. 5A and 5B are enlarged operational views of an elastic lock block shown in FIG. 3.
Figure 5B:
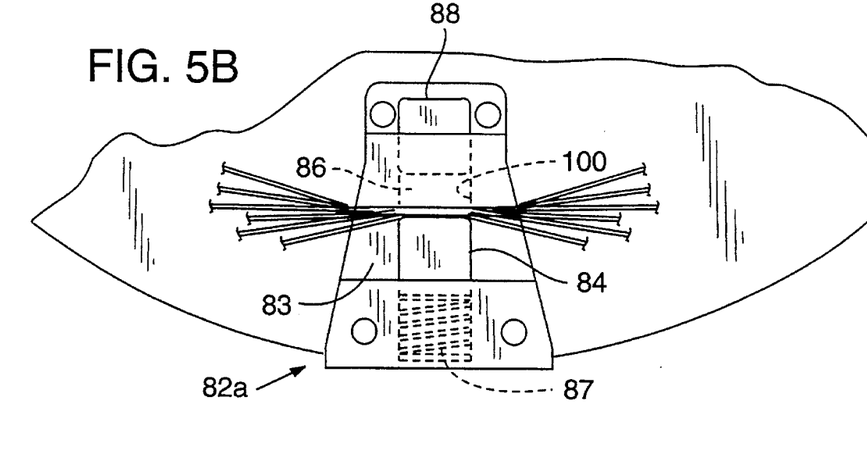

Exemplary lock block 82a, as shown in FIGS. 3, 7, 5A and 5B, has a slot-like holding bay 83 that opens outwardly to receive the elastic bands 24a–24f guided from the leading guide members 80a. As best shown in FIGS. 5A and 5B, a locking pin, or member, 84 having a notch 86 extends through a bore 85 defined in the lock block and is actuable to grip the bands 24a–24f within bay 83. The locking pin 84 rests in contact with a coil spring 87 to normally bias the pin upwardly toward a lock position as shown in FIG. 5B. In the lock position, the notch 86 in pin 84 moves into an upper portion of the bore 85, and the top 88 of the pin 84 protrudes from the top of the lock block 82a.

To receive the elastic bands, a stationary cam 90 depresses the locking pin top 88 such that the pin notch 86 moves downwardly into alignment with the bay 83 to receive the bands 24a–24f (see FIGS. 3 and 5A). The holding bay 83 is relatively wide to receive the bands 24a–24f, which radiate in the directions of the leading and trailing guide members 80a, 81a. As shown in FIG. 3, the cam 90 may be fixed on a stationary support member 92 to depress the locking pin 84 as the applicator 70 rotates to thread elastic between the leading 80a and trailing 81a positioning members. The cam may have an arcuate profile to actuate the lock block mechanism 82a as the end wheel 72a rotates. Once the bands are received in the bay 83, the cam 90 releases the pin 84 to return to the lock position wherein the bands are gripped between the bottom of the notch 86 and the top of the bay 83 as seen in FIG. 5B.

Referring again to FIG. 7, the interval of rotation from position 1 to position 2 threads the bands through the lock block mechanism 82a and brings the feeder head 69 adjacent the trailing set of guide members 81a.

The applicator rotation then is halted, and the feeder head 69 is swung from position 2 through the arcuate path 68 to position 3, whereby the bands 24a–24f are threaded through the trailing guide members 81a and the leading guide members 80b. The structure of the feeder head 69 will now be described in relation to such threading.

Figure 4:
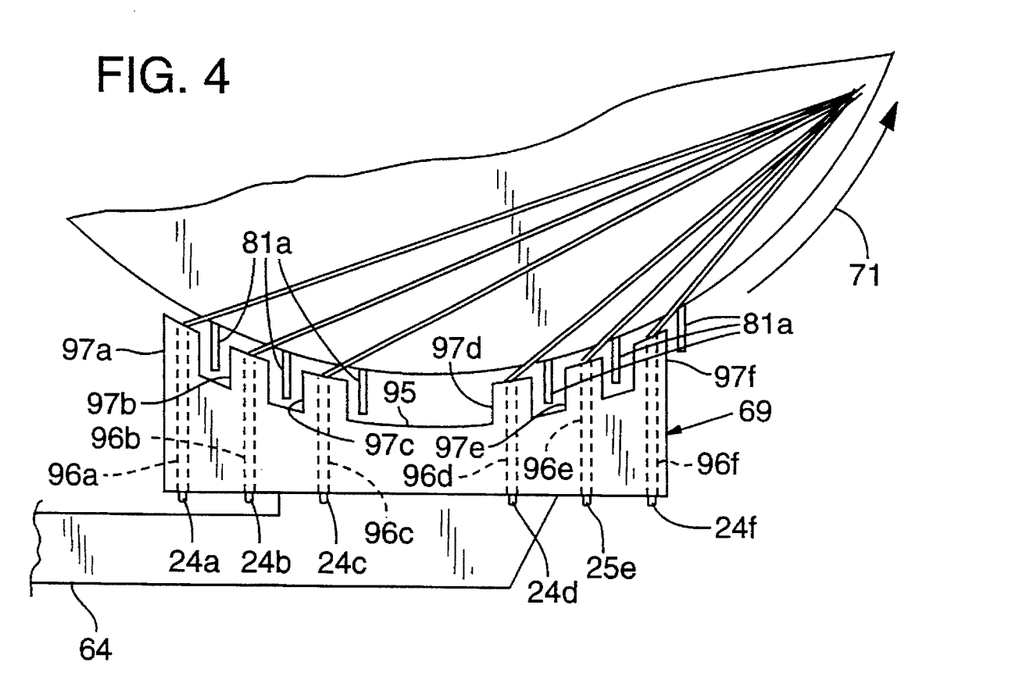
FIG. 4 is an enlarged, cut-away view of the bottom portion of FIG. 3.

As best shown in FIG. 4, the feeder head 69 is block-shaped with a concave upper surface 95 for close positioning adjacent the end wheels 72a, 72b. Six elastic guide apertures 96a, 96b, 96c, 96d, 96e, 96f extend vertically through the head 69. The head upper surface has six protruding feeder fingers 97a, 97b, 97c, 97d, 97e, 97f through which the elastic guide apertures respectively extend to apply the elastic bands 24a, 24b, 24c, 24d, 24e, 24f. The elastic bands are threaded into the respective guide apertures at the feeder head bottom and extend from the feeder fingers.

As the feeder head 69 sweeps from position 2 to position 3, the feeder fingers 97a–97f interdigitate with the trailing guide members 81a to thread the bands 24a–24f around the upstream sides of the guide members 81a, and interdigitates with the aligned set of leading guide members 80b on the opposing end wheel 72b to thread the bands around the downstream sides of the guide members 80b. The bands extend in tension transverse to the flow path 20 between the members 81a and 80b.

As is shown in FIG. 7, such "upstream" and "downstream" threading of bands permits the guide members to support the bands 24a–24f in the square wave pattern. To support the bands in the square wave pattern, grouped sets of leading guide members, lock blocks, and trailing guide members on each end wheel are staggered relative to those on the opposing end wheel. To permit the upstream and downstream threading, the guide members 81a and 80b (and 80a and 81b) that support the same transverse lengths of elastic bands 24a–24f are slightly offset along the peripheries of the end wheels.

Once the feeder head 69 reaches the end of the arcuate path 68, as at position 3, the applicator 70 rotates through another 60 degree interval in moving from position 3 to position 4. The applicator rotation threads the bands from the leading guide members 80b through lock block 82b and brings the trailing guide members 81b adjacent the feeder head 69 at position 4.

The applicator rotation halts at position 4, and the feeder head 69 swings back through the arcuate path 68 to position 5. In swinging from position 4 to position 5, the bands 24a–24f are threaded in stretched tensioned condition around the upstream side of the trailing members 81b, and around the downstream side of leading members 80a.

Such cooperative feeder head swinging, and applicator rotation through 60 degree intervals, continues as machine operation continues. Known rotary drive mechanism is operatively connected to axle 74 to produce the desired intermittent rotation of the applicator.

The square wave pattern of bands 24a–24f is intermittently rotated along applicator path 71 to be deposited on the backing sheet 12 at nip 73. The bands extend in tension from the leading and trailing sets of guide members through the respective guide blocks 82a, 82b. As shown in FIGS. 3 and 7, cutting blades 98 are mounted inboard of the end wheels 72a, 72b adjacent the nip 73 to sever the gripped elastic bands adjacent the edges of the backing sheet 12. The bands 24a–24f are deposited on the adhesive-coated backing sheet 12 slightly in advance of the cutting of the elastic bands at the nip 73.

As shown in FIG. 3, the lock blocks 82a, 82b hold the severed end portions of the elastic until a second cam 91 actuates the lock block mechanism to release the elastic, which is then sucked into a vacuum 93 for disposal.

Figure 6:
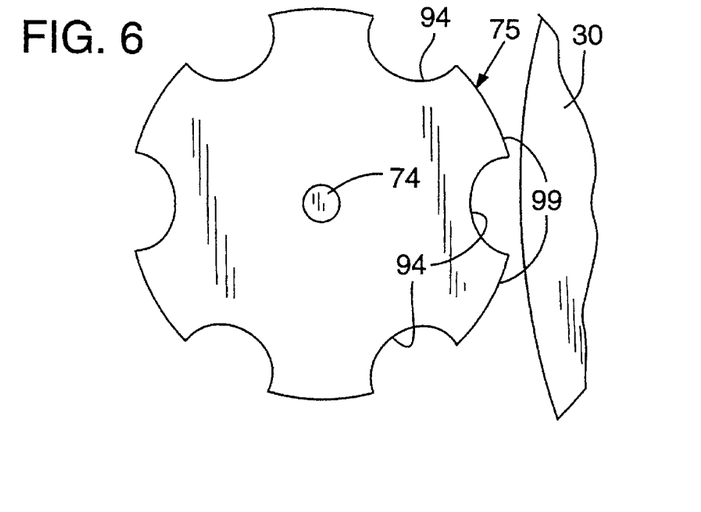
FIG. 6 is an enlarged cut-away view taken generally along the line 6—6 in FIG. 2.

The elastic bands are pressed against the backing sheet and the adhesive previously applied thereto at nip 73 by the tension of the elastic and by the four rotating pressure disks 75 as shown in FIGS. 2 and 6. The pressure disks 75 have six protruding radial portions 99 that define an intermittently broken circular profile. The radial portions 99 are aligned with the sets of guide members such that the radial portions 99 press the elastic bands 24a–24f against the backing sheet 12 at nip 73. The pressure disks 75 are recessed in regions 94 between radial portions 99 such that the disks do not contact the adhesive-coated backing sheet 12 when elastic bands are not being applied. The accumulation of adhesive on the pressure disks 75 is thereby minimized.

As best seen in FIG. 1, the backing sheet 12 carrying the applied bands of elastic rotates with the conveyor drum 30 to nip 39, where the elastic bands 24a–24f and absorbent pads 14 are encased between the backing sheet 12 and the liner sheet 16. The bumper 38a on the nip roller 38 tightly pinches the elastic bands between the sheets 12, 16 to provide secure adhesion.

First Alternate Elastic Feeder

Figure 8:
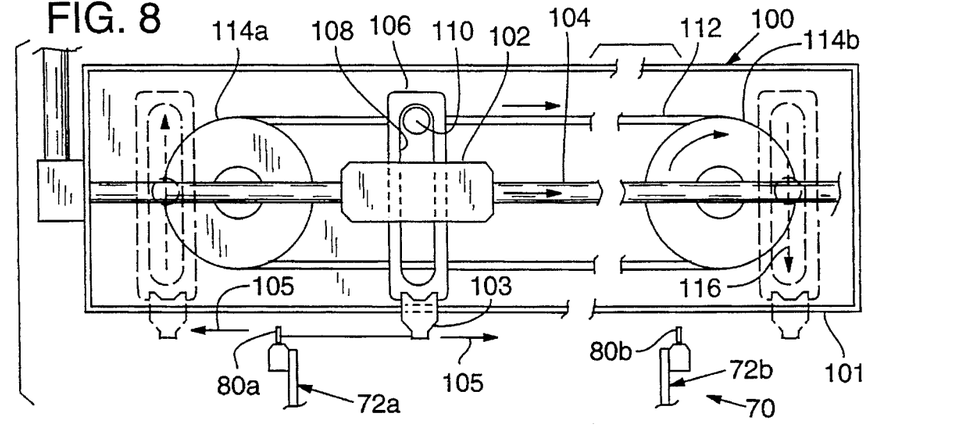
FIG. 8 is an elastic feeder in accordance with an alternate embodiment of the invention.

FIG. 8 shows an alternate form of elastic band feeder 100, which may be used in place of feeder head 69, supported by a housing 101 that is mounted adjacent elastic applicator 70. A translator member 102 supporting a feeder head 103 is slidably mounted on a support shaft 104 for reciprocating movement therealong. Reciprocation of the translator member 102 moves the feeder head 103 reciprocatively through a linear feeder path 105 to thread elastic onto the end wheels 72a, 72b of the elastic applicator 70, as previously described in relation to operation of feeder head 69.

The translator member 102 is tubular with an interior bearing surface for smooth sliding translation along support shaft 104. A link member 106 fixedly extends outwardly from the translator member 102 and is slidably connected to a drive belt 112 that is trained about a pair of drive pulleys 114a, 114b. The link member 106 has an elongate central slot 108 extending laterally of support shaft 104. Slot 108 slidably receives a drive pin 110 that is secured to belt 112. The drive pin 110 drags translator member 102 along support rod 104 as pin 110 moves with belt 112 between the pulleys. The drive pin 110 moves linearly within the link member slot 108 as the drive pin 110 rounds either of the pulleys 114a, 114b (see dashed link members 106). The drive pin 110 then moves in the opposite direction between the pulleys, dragging the link member 106 in the opposite direction along the support rod 104.

The pulleys 114a, 114b are respectively mounted outboard of the end wheels 72a, 72b of the elastic applicator 70. The drive pin 110 movement through the slot 108 as the pin 110 rounds the pulleys causes the feeder head 103 to slow and momentarily stop at either end of the linear path 105.

Feeder head 103 may have essentially the same structure as the feeder head 69 shown in FIG. 4. The elastic applicator 70 moves in the same intermittent fashion as described relative to FIG. 7, to permit the feeder head 103 to thread elastic thereon.

Second Alternate Elastic Feeder

Figure 9:
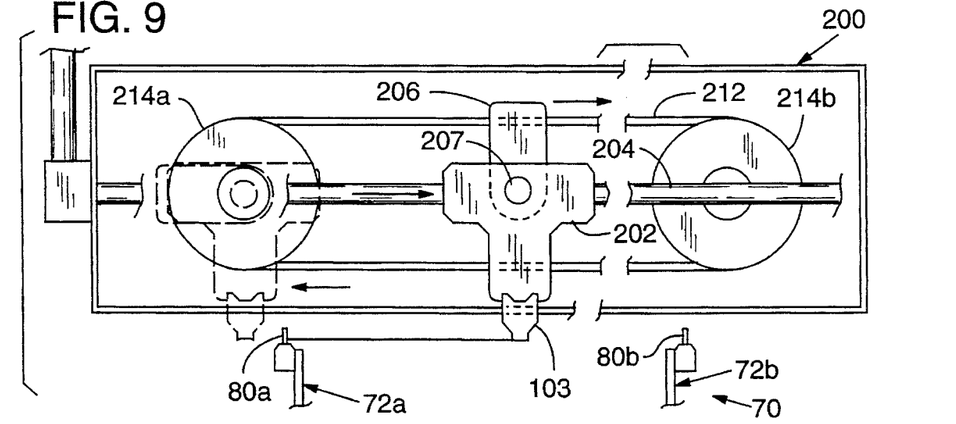
FIG. 9 is an elastic feeder in accordance with a second alternate embodiment of the invention.

FIG. 9 shows a second alternate feeder 200, having a tubular translator member 202 reciprocatively moving along support shaft 204. In this embodiment, the drag link 206 is pivotally attached adjacent one of its ends to the translator member 202 by pivot pin 207, and is fixed to the drive belt 212. The drag link drags the translator member 202 in one direction along the support shaft as the drag link moves with the belt 212 between the pulleys 214a, 214b. The drag link 206 pivots about the pivot pin 207 as it moves on the belt about either of the pulleys 214a, 214b. The drag link then drags the translator member in the opposite direction along the support shaft. The translator member 202 is substantially stationary during the movement of the drag link about pulleys 214a, 214b.

Third Alternate Elastic Feeder

Figure 10:
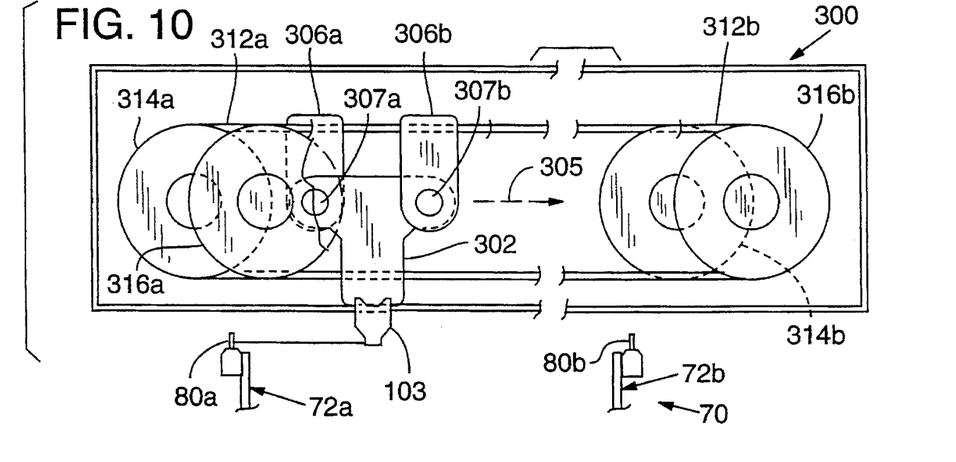
FIG. 10 is an elastic feeder in accordance with a third alternate embodiment of the invention.

FIG. 10 shows another elastic feeder 300 that uses two drag links 306a, 306b. No support shaft is required. The drag links 306a, 306b are pivotally connected by about pivot pins 307a, 307b to laterally spaced positions on a T-shaped translator member 302. The drag links 306a, 306b are respectively fixed on independent drive belts 312a, 312b, which run on opposite sides of the translator member 302. Belt 312a is trained about a pair of pulleys 314a, 314b, and belt 312b is trained about a pair of pulleys 316a, 316b. The sets of pulleys 314a, 314b and 316a, 316b are offset by a distance equal to the spacing of the pivot pins 307a, 307b on the translator member. The belts run in the same direction.

The dual drag link 306a, 306b construction stably holds the translator member 302 for linear movement along a path 305. The drag links 306a, 306b move in parallel and extend in the same direction from the translator member 302. The drag links carry the translator member 302 along the linear path 305 as they move respectively on the belts 312a, 312b between their respective pulleys. The drag links pivot in unison as they move about their respective pulleys. The offset between the drag links and between the pulleys mounting the belts permits the drag links to pivot in unison while maintaining the desired orientation of the translator member.

The drag links 306a, 306b could alternatively extend in opposing parallel directions from the translator member if the drive belts 312a, 312b are run in opposite directions.

The foregoing has been described in connection with preferred and alternative embodiments. It will be appreciated by one of ordinary skill in the art, however, that various modifications and variations may be substituted for the mechanisms described herein while remaining defined by the appended claims and their equivalents.

I claim:

1. A method for applying elongate tensioned elastic to material moving along a flow path with the elastic extending transversely of the flow path comprising the steps of:

moving said material in one direction along said flow direction;

providing a quantity of elongate elastic;

drawing an elongate section of elastic from such reservoir of elastic;

stretching said section of elastic to a desired tension;

feeding said elastic reciprocatively in a feeder path that is substantially transverse of the flow path and has opposed ends adjacent opposite sides of the flow path;

grasping transverse portions of said elastic at spaced apart regions adjacent the opposed ends of the feeder path as the elastic is reciprocatively fed along the feeder path;

moving said transverse portions along an applicator path to the flow path while maintaining the transverse portions extending transversely of the flow path;

depositing the transverse portions onto the material while further stretching the transverse portions and maintaining a selected spacing between the transverse portions relative to the flow path; and cutting the transverse portions inboard of the spaced apart regions to sever the transverse portions from remainder portions of the elastic.

2. The method of claim 1, including the step of:

providing an elastic applicator that is operable to grasp said transverse portions of elastic when the applicator is rotated about an axis substantially parallel with the feeder path; and rotating the elastic applicator when the elastic is being fed adjacent the opposing ends of the feeder path.

3. The method of claim 2, further including the step of halting said rotation of the elastic applicator when the elastic is being fed in a central region between the opposing ends of the feeder path.

4. The method of claim 1, wherein the step of grasping the transverse portions includes:

threading the spaced apart regions about guides such that the opposing elastic regions extend substantially perpendicular to the transverse elastic portions and have selected lengths that define the spacing between adjacent transverse portions.

5. The method of claim 1, wherein the step of feeding the elastic comprises:

providing an elastic feeder head movable transversely of the flow path and mounted distally on a swing arm; and swinging the swing arm to move the feeder head reciprocatively along the feeder path while the feeder head is feeding elastic.

6. A method for applying elongate tensioned elastic to material moving along a flow path with the elastic extending transversely of the flow path comprising the steps of:

moving said material in one direction along said flow path;

providing a quantity of elongate elastic supplying a plurality of elastic bands;

drawing an elongate section of the elastic bands from such supply of elastic bands;

stretching said section of elastic bands to a desired tension;

defining an elastic feeder path extending transverse of the flow path;

grasping a first region of said elastic bands at a single position adjacent a first end of the feeder path spaced laterally to one side the flow path;

feeding a first transverse portion of said elastic bands in a first direction across the feeder path away from said first end;

grasping a second region of said plurality of elastic bands at a single position adjacent the second end of the flow path to define a length of the first transverse elastic portion;

moving said first transverse portion and said first and second region along an applicator path perpendicular to said feeder path and toward the flow path while maintaining said first transverse portion transverse to the flow path;

depositing the transverse portion onto the material; and cutting the transverse portion inboard of the spaced apart first and second regions.

7. Apparatus for applying elongate tensioned elastic to material moving along a flow path with the elastic extending transversely of the flow path comprising:

a first conveyor having an outer conveyor face for carrying material in one direction along the flow path;

elastic storage for holding a quantity of elongate elastic;

an elastic conveyor operable to draw elastic from said storage and move the elastic longitudinally;

an elastic tensioning device positioned along the elastic conveyor and through which the elastic is conveyed, the tensioning device operable to stretch the elastic conveyed along the elastic conveyor;

a transverse elastic applicator receiving elastic substantially continuously from the elastic conveyor, the elastic applicator being positioned adjacent the first conveyor and movable toward the flow path, the elastic applicator having enlarged opposing end portions with spaced guide members mounted thereon outboard of opposite sides of the first conveyor to hold tensioned elastic suspended therebetween and transversely of the flow path, the enlarged end portions and guide members operable to hold the elastic in suspended tensioned position as the elastic applicator moves the elastic to the flow path, the elastic applicator receiving the first conveyor between the opposing enlarged end portions and guide members such that the opposing enlarged end portions overlap the opposite sides of the first conveyor and the first conveyor presses against the suspended elastic to further stretch the elastic between the enlarged end portions as the elastic applicator applies the elastic to the material on the first conveyor; and cutters positioned inboard of the guide members operable to sever the elastic from the positioning members after it has been applied to the material.

8. The apparatus of claim 7, further comprising an adhesive applicator operable to apply adhesive to secure the elastic to the material.

9. The apparatus of claim 7, wherein the elastic applicator is mounted for rotation about an axis transverse of the flow path, the enlarged end portions have selected diameters, and a pressure plate is mounted for rotation intermediate the enlarged end portions, the pressure plate having a plate diameter less than the selected end portion diameters.

10. The apparatus of claim 7, which further comprises an elastic feeder positioned adjacent the elastic applicator having a feeder head operable to thread elastic onto the guide members, the feeder head being reciprocatively movable transversely of the flow path across the elastic applicator to thread elastic onto the guide members in a square-wave pattern.

11. The apparatus of claim 10, wherein:
   the guide members extend outwardly from the elastic applicator and are arranged in sets that are adjacent opposite sides of the flow path; and
   the feeder head has protruding feeder fingers from which elastic extends, the feeder fingers interdigitating with sets of guide members as the feeder head reciprocatively moves adjacent the elastic applicator to thread elastic onto the guide members.

12. The apparatus of claim 10, wherein the elastic applicator further comprises a drive that intermittently moves the elastic applicator when the feeder head is outboard of the guide members, and halts the elastic applicator when the feeder head moves transversely to thread elastic onto the guide members.

13. The apparatus of claim 10, wherein the elastic comprises a plurality of elastic bands and the elastic feeder head is operable to thread the plurality of elastic bands between the opposing sets of guide members on the opposing enlarged end portions, and a lock block is mounted on the elastic applicator between adjacent sets of guide members, the lock block having an outwardly opening holding bay operable to receive the plurality of elastic bands that extend between adjacent sets of members, and a locking member operable to engage and hold elastic bands received in said bay.

14. The apparatus of claim 13, wherein the locking member is received within a bore in the lock block, the locking member having a notch that is alignable with the holding bay when in an open position to permit reception of elastic bands, and a biasing member operable to bias the locking member to a lock position wherein the notch is offset from the holding bay to grasp elastic bands held in the holding bay.

15. The apparatus of claim 14, wherein a portion of the locking member extends from the lock block when in the lock position, and a cam mechanism positioned adjacent the elastic applicator is operable to shift the locking member into the lock block to the open position.

16. Apparatus for applying elongate tensioned elastic to material moving along a flow path with the elastic extending transversely of the flow path comprising:
   a first conveyor for carrying material in one direction along the flow path;
   elastic storage for carrying a quantity of elongate elastic supplying a plurality of elastic bands;
   an elastic conveyor operable to draw elastic from said storage and move the elastic longitudinally;
   an elastic tensioning device positioned along the elastic conveyor and through which the elastic is conveyed, the tensioning device operable to stretch the elastic as the elastic is conveyed along the elastic conveyor;
   an elastic feeder receiving the plurality of elastic bands from the elastic conveyor and having a feeder head that is reciprocatively movable in a feeder path extending transverse of the flow path; and
   an elastic applicator positioned adjacent the feeder head, the elastic applicator operable to move substantially perpendicular of the feeder path and toward the flow path, the feeder head operable to thread the plurality of elastic bands onto the elastic applicator such that the elastic bands extend in tension transverse to the flow path, the elastic applicator having lock blocks on opposing sides of the applicator, the lock blocks each having a holding bay for receiving and holding the plurality of elastic bands, and the elastic applicator moving the tensioned elastic bands to the flow path to deposit the elastic bands onto the material on the first conveyor; and
   cutters positioned adjacent the first conveyor to sever the deposited elastic bands.

17. The apparatus of claim 16, further comprising a drive that is coupled to the elastic applicator and intermittently moves the elastic applicator when the feeder head is positioned at either end of the reciprocative feeder path, and the drive halting the elastic applicator when the feeder head moves through an intermediate portion of the reciprocative feeder path such that the feeder head threads elastic bands onto the elastic applicator in a square-wave pattern.

18. The apparatus of claim 16, wherein the elastic feeder includes a pivotable swing arm that swings the feeder head so that the feeder path is arcuate.

19. The apparatus of claim 16, wherein the elastic feeder includes a feeder head mounted on a translator that reciprocatively moves along a linear path extending transversely of the flow path.

20. The apparatus of claim 19, wherein the translator has a pivotable drag link fixed to a drive belt trained about a pair of pulleys, the drag link moving with the drive belt to move the translator reciprocatively along the linear path.

21. The apparatus of claim 19, wherein the translator is slidably mounted on a support shaft that extends along the linear path.

22. The apparatus of claim 16, wherein the elastic applicator is mounted for rotation about an axis extending transversely of the flow path, the elastic applicator having generally circular opposing end wheels that rotate about the axis and have protruding guide members operable to receive elastic bands from the feeder head and position the elastic bands on the elastic applicator.

23. The apparatus of claim 22, wherein the feeder head has a concave profile that conforms to an arc of the circular shape of the end wheels so that the feeder head may be closely positioned to the end wheels during threading of elastic bands onto the elastic applicator.

24. The apparatus of claim 22, wherein the elastic applicator includes a pressure plate mounted intermediate the end wheels, the pressure plate rotating about the axis and having a peripheral surface defining a circular profile operable to press the elastic bands onto the material carried on the first conveyor.

25. The apparatus of claim 24, wherein the peripheral surface of the pressure plate has recessed portions recessed from the circular profile, the recessed portions operable such that the pressure plate is intermittently spaced from the first conveyor as the pressure plate rotates.

26. The apparatus of claim 24, wherein the end wheels have a diameter greater than the diameter of the pressure plate circular profile so as to overlap the first conveyor and stretch the elastic.

27. Apparatus for applying elongate tensioned elastic to material moving along a flow path with the elastic extending transversely of the flow path comprising:

a first conveyor for carrying material in one direction along the flow path;

elastic storage for supplying a quantity of elongate elastic supplying a plurality of elastic bands;

an elastic conveyor operable to draw the elastic from said storage and move the elastic longitudinally;

an elastic tensioning device positioned along the elastic conveyor and through which the elastic is conveyed, the tensioning device operable to stretch the elastic as the elastic is conveyed along the elastic conveyor;

an elastic feeder receiving the plurality of elastic bands from the elastic conveyor and having a feeder head that is reciprocatively movable in a feeder path extending transverse of the flow path, the feeder head having a concave profile; and a rotatable elastic applicator positioned adjacent the feeder head, the elastic applicator defining a circular profile complementary to the concave profile of the feeder head, the feeder head concave profile being closely spaced to the elastic applicator circular profile as the feeder head moves in the feeder path, the elastic applicator operable to move substantially perpendicular of the feeder path and toward the flow path, the feeder head operable to thread the plurality of elastic bands onto the elastic applicator such that the elastic bands extend in tension transverse to the flow path, and the elastic applicator moving the tensioned elastic bands to the flow path to deposit the elastic bands onto the material on the first conveyor; and cutters positioned adjacent the first conveyor to sever the deposited elastic bands.

* * * * *